United States Patent
Banet et al.

(10) Patent No.: US 9,149,192 B2
(45) Date of Patent: Oct. 6, 2015

(54) SYSTEM FOR MEASURING VITAL SIGNS USING BILATERAL PULSE TRANSIT TIME

(75) Inventors: Matthew John Banet, Del Mar, CA (US); Michael James Thompson, San Diego, CA (US); Zhou Zhou, La Jolla, CA (US); Henk Visser, II, San Diego, CA (US); Robert Kenneth Hunt, Vista, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 1890 days.

(21) Appl. No.: 11/420,652

(22) Filed: May 26, 2006

(65) Prior Publication Data
US 2007/0276632 A1 Nov. 29, 2007

(51) Int. Cl.
*A61B 5/02* (2006.01)
*A61B 5/021* (2006.01)
*A61B 5/00* (2006.01)
A61B 5/024 (2006.01)
(Continued)

(52) U.S. Cl.
CPC .............. *A61B 5/021* (2013.01); *A61B 5/02125* (2013.01); *A61B 5/02438* (2013.01); *A61B 5/6826* (2013.01); *A61B 5/6838* (2013.01); A61B 5/0245 (2013.01); A61B 5/02416 (2013.01); A61B 5/1455 (2013.01); A61B 5/7239 (2013.01); A61B 2560/0462 (2013.01); A61B 2560/0468 (2013.01)

(58) Field of Classification Search
CPC ............... A61B 5/02125; A61B 5/021; A61B 5/02416; A61B 5/02438; A61B 5/0245; A61B 5/1455; A61B 5/6826; A61B 5/6838; A61B 5/7239

USPC .................. 600/300–301, 485, 500, 504, 507
See application file for complete search history.

(56) References Cited

U.S. PATENT DOCUMENTS

| 3,412,729 A | 11/1968 | Smith |
| 4,063,551 A | 12/1977 | Sweeny |

(Continued)

OTHER PUBLICATIONS

Assessment of Vasoactive Agents and Vascular Aging by the Second Derivative of Photoplethysmogram Waveform, Takazawa et. al, Hypertension 32: 365-370, 1998.

(Continued)

*Primary Examiner* — Navin Natnithithadha
*Assistant Examiner* — Eric Messersmith
(74) *Attorney, Agent, or Firm* — Michael A. Whittaker; Acuity Law Group, P. C.

(57) ABSTRACT

The invention provides a monitor for measuring blood pressure and other vital signs from a patient without using a cuff. The invention provides a hand-held device for measuring vital signs (e.g. blood pressure) from a patient that features: i) a housing that encloses a first sensor, that includes a first electrode and a first optical system configured to generate a first optical signal; ii) a second sensor that includes a second electrode and a second optical system configured to generate a second optical signal; iii) an amplifier system, in electrical contact with the first and second electrodes, configured to processes electrical signals from the first and second electrodes to generate an electrical waveform; and iv) a microprocessor, in electrical communication with the amplifier system, first optical system, and second optical system, the microprocessor configured to process the electrical waveform and first and second optical signals with an algorithm to determine at least one of the patient's vital signs.

7 Claims, 5 Drawing Sheets

(51) Int. Cl.
*A61B 5/0245* (2006.01)
*A61B 5/1455* (2006.01)

(56) References Cited

U.S. PATENT DOCUMENTS

| | | | |
|---|---|---|---|
| 4,080,966 A | 3/1978 | McNally et al. | |
| 4,245,648 A | 1/1981 | Trimmer et al. | |
| 4,320,767 A | 3/1982 | Villa-Real | |
| 4,367,752 A | 1/1983 | Jimenez et al. | |
| 4,380,240 A | 4/1983 | Jobsis et al. | |
| 4,425,920 A | 1/1984 | Bourland et al. | |
| 4,681,118 A | 7/1987 | Asia et al. | |
| 4,777,954 A | 10/1988 | Keusch et al. | |
| 4,825,879 A | 5/1989 | Tan et al. | |
| 4,846,189 A | 7/1989 | Sun | |
| 4,869,261 A | 9/1989 | Penaz | |
| 4,917,108 A | 4/1990 | Mault | |
| 5,002,055 A | 3/1991 | Merki et al. | |
| 5,038,792 A | 8/1991 | Mault | |
| 5,054,494 A | 10/1991 | Lazzaro et al. | |
| 5,111,817 A | 5/1992 | Clark et al. | |
| 5,140,990 A | 8/1992 | Jones et al. | |
| 5,178,155 A | 1/1993 | Mault | |
| 5,179,958 A | 1/1993 | Mault | |
| 5,213,099 A | 5/1993 | Tripp, Jr. | |
| 5,237,997 A | 8/1993 | Greubel et al. | |
| 5,309,916 A | 5/1994 | Hatschek | |
| 5,316,008 A * | 5/1994 | Suga et al. | 600/513 |
| 5,368,039 A | 11/1994 | Moses | |
| 5,435,315 A | 7/1995 | McPhee et al. | |
| 5,485,848 A | 1/1996 | Jackson et al. | |
| 5,551,438 A | 9/1996 | Moses | |
| 5,632,272 A | 5/1997 | Diab et al. | |
| 5,727,558 A | 3/1998 | Hakki et al. | |
| 5,743,857 A | 4/1998 | Shinoda et al. | |
| 5,788,634 A | 8/1998 | Suda et al. | |
| 5,836,300 A | 11/1998 | Mault | |
| 5,857,975 A | 1/1999 | Golub | |
| 5,865,755 A | 2/1999 | Golub | |
| 5,865,758 A | 2/1999 | Louzianine | |
| 5,891,042 A | 4/1999 | Sham et al. | |
| 5,921,936 A | 7/1999 | Inukai et al. | |
| 6,004,274 A | 12/1999 | Nolan et al. | |
| 6,013,009 A | 1/2000 | Karkanen | |
| 6,050,940 A | 4/2000 | Braun et al. | |
| 6,120,456 A * | 9/2000 | Oka et al. | 600/485 |
| 6,120,459 A * | 9/2000 | Nitzan et al. | 600/493 |
| 6,176,831 B1 | 1/2001 | Voss et al. | |
| 6,224,548 B1 | 5/2001 | Gopinathan et al. | |
| 6,245,014 B1 | 6/2001 | Brainard, II | |
| 6,272,936 B1 | 8/2001 | Oreper | |
| 6,280,390 B1 | 8/2001 | Akselrod et al. | |
| 6,334,065 B1 | 12/2001 | Al-Ali et al. | |
| 6,336,900 B1 | 1/2002 | Alleckson et al. | |
| 6,364,842 B1 | 4/2002 | Amano et al. | |
| 6,371,921 B1 | 4/2002 | Caro et al. | |
| 6,375,614 B1 | 4/2002 | Braun et al. | |
| 6,398,727 B1 | 6/2002 | Bui et al. | |
| 6,413,223 B1 | 7/2002 | Yang et al. | |
| 6,432,061 B1 | 8/2002 | Nissila et al. | |
| 6,443,905 B1 | 9/2002 | Nissila et al. | |
| 6,443,906 B1 | 9/2002 | Ting et al. | |
| 6,475,146 B1 | 11/2002 | Frelburger et al. | |
| 6,475,153 B1 | 11/2002 | Khair et al. | |
| 6,477,397 B1 | 11/2002 | Ronkainen et al. | |
| 6,511,436 B1 | 1/2003 | Asmar | |
| 6,514,211 B1 | 2/2003 | Baura | |
| 6,527,711 B1 | 3/2003 | Stivoric et al. | |
| 6,533,729 B1 | 3/2003 | Khair et al. | |
| 6,537,225 B1 * | 3/2003 | Mills | 600/481 |
| 6,546,269 B1 | 4/2003 | Kurnik | |
| 6,553,247 B1 | 4/2003 | Rytky | |
| 6,556,852 B1 | 4/2003 | Schulze et al. | |
| 6,558,321 B1 | 5/2003 | Burd et al. | |
| 6,571,200 B1 | 5/2003 | Mault | |
| 6,595,929 B2 | 7/2003 | Stivoric et al. | |
| 6,599,251 B2 | 7/2003 | Chen et al. | |
| 6,605,038 B1 | 8/2003 | Teller et al. | |
| 6,605,044 B2 | 8/2003 | Bimbaum | |
| 6,609,023 B1 | 8/2003 | Fischell et al. | |
| 6,612,984 B1 | 9/2003 | Kerr, II | |
| 6,616,613 B1 | 9/2003 | Goodman | |
| 6,645,154 B2 | 11/2003 | Oka | |
| 6,645,155 B2 | 11/2003 | Inukai et al. | |
| 6,652,466 B2 | 11/2003 | Sugo et al. | |
| 6,678,543 B2 | 1/2004 | Diab et al. | |
| 6,681,454 B2 | 1/2004 | Modgil et al. | |
| 6,714,804 B2 | 3/2004 | Al-Ali et al. | |
| 6,723,054 B1 | 4/2004 | Baruch et al. | |
| 6,733,447 B2 | 5/2004 | Lai et al. | |
| 6,740,045 B2 | 5/2004 | Amano | |
| 6,755,792 B2 * | 6/2004 | Masuda et al. | 600/500 |
| 6,775,566 B2 | 8/2004 | Nissila | |
| 6,808,473 B2 | 10/2004 | Hisano et al. | |
| 6,813,511 B2 | 11/2004 | Diab et al. | |
| 6,814,705 B2 | 11/2004 | Kawaguchi | |
| 6,852,083 B2 | 2/2005 | Caro et al. | |
| 6,871,084 B1 | 3/2005 | Kigsley et al. | |
| 6,893,401 B2 * | 5/2005 | Chen et al. | 600/485 |
| 2002/0042558 A1 * | 4/2002 | Mendelson | 600/323 |
| 2002/0183627 A1 | 12/2002 | Nishii et al. | |
| 2004/0030261 A1 | 2/2004 | Rantala | |
| 2004/0260186 A1 | 12/2004 | Dekker | |
| 2006/0074332 A1 * | 4/2006 | Bischoff et al. | 600/515 |
| 2006/0195035 A1 * | 8/2006 | Sun | 600/503 |
| 2009/0216132 A1 * | 8/2009 | Orbach | 600/485 |

OTHER PUBLICATIONS

'Pulse transit time measured from the ECG: an unreliable marker of beat-to-beat blood pressure', Payne et. al, J. Appl. Physiol 100: 136-141, 2006.

Weijia Cui, Lee E. et el., In Vivo Reflectance of Blood and Tissue as a Function of Light Wavelength, submitted to IEEE Transactions on Biomedical Engineering, vol. 37 No. 6.

* cited by examiner

SYSTEM FOR MEASURING VITAL SIGNS USING BILATERAL PULSE TRANSIT TIME

STATEMENT REGARDING FEDERALLY SPONSORED RESEARCH OR DEVELOPMENT

Not Applicable

BACKGROUND OF THE INVENTION

1. Field of the Invention

The present invention relates to a system for measuring vital signs, particularly blood pressure, featuring a hand-held, cuffless vital sign monitor.

2. Description of Related Art

Pulse oximeters are medical devices featuring an optical module, typically worn on a patient's finger or ear lobe, and a processing module that analyzes data generated by the optical module. The optical module typically includes first and second light sources (e.g., light-emitting diodes, or LEDs) that transmit optical radiation at, respectively, red ($\lambda \sim 600$-$700$ nm) and infrared ($\lambda \sim 800$-$1200$ nm) wavelengths. The optical module also features a photodetector that detects transmitted radiation that passes through an underlying artery within, e.g., the patient's finger or earlobe. Typically the red and infrared LEDs sequentially emit radiation that is partially absorbed by blood flowing in the artery. The photodetector is synchronized with the LEDs to detect the transmitted radiation. In response, the photodetector generates a separate radiation-induced signal corresponding to each wavelength. The signal, called a plethysmograph, varies in a time-dependent manner as each heartbeat varies the volume of arterial blood and hence the amount of radiation absorbed along the path of light between the LEDs and the photodetector. A microprocessor in the pulse oximeter digitizes and processes plethysmographs generated by the red and infrared radiation to determine the degree of oxygen saturation in the patient's blood using algorithms known in the art. A number between 94%-100% is considered normal, while a number below 85% typically indicates the patient requires hospitalization. In addition, the microprocessor analyzes time-dependent features in the plethysmograph to determine the patient's heart rate.

Another medical device called an electrocardiograph features conductive electrodes, placed at various locations on a patient's body, that measure electrical signals which pass into an amplification circuit. The circuit generates a waveform called an electrocardiogram, or ECG, that describes a time-dependent response of the patient's cardiovascular system.

Various methods have been disclosed for using both plethysmographs and ECGs, taken alone or in combination, to measure arterial blood pressure. One such method is disclosed in U.S. Pat. No. 5,140,990 to Jones et al. The '990 patent discloses using a pulse oximeter with a calibrated auxiliary blood pressure measurement to generate a constant that is specific to a patient's blood pressure.

Another method for using a pulse oximeter to measure blood pressure is disclosed in U.S. Pat. No. 6,616,613 to Goodman. The '613 patent discloses processing a pulse oximetry signal in combination with information from a calibrating device to determine a patient's blood pressure.

U.S. Pat. Nos. 5,857,795 and 5,865,755 to Golub each discloses a method and device for measuring blood pressure that processes a time difference between points on an optical plethysmograph and an ECG along with a calibration signal.

U.S. Pat. No. 6,511,436 to Asmar discloses a device for evaluating arterial wall stiffness by using pulse wave velocity measurements. The device estimates blood pressure using pulse wave velocity and a patient's biometric parameters.

Chen et al, U.S. Pat. No. 6,599,251, discloses a system and method for monitoring blood pressure by detecting plethysmographs at two different locations on a subject's body, preferably on the subject's finger and earlobe. The plethysmographs are detected using conventional pulse oximetry devices and then processed to determine blood pressure.

Inukai et al., U.S. Pat. No. 5,921,936, discloses a system that uses an electrocardiogram to detect the start of a heart beat and uses a cuff equipped with a pressure sensor to detect pulse waves in order to calculate a pulse transit time.

Suda et al., U.S. Pat. No. 5,788,634, describes a multi-purpose, clip-on sensor featuring a 'gripper' that includes an electrode pair and an optical system operating in a transmission mode. The electrode pair and optical system generate information that is processed outside of the sensor to make a blood pressure measurement.

Baruch et al., U.S. Pat. No. 6,723,054, describes an arm-worn system featuring two optical systems that measure two independent signals from a patient's arm. A processor calculates mathematical derivatives of the signals to derive a pulse transit time which can be used to calculate blood pressure.

Suga et al., U.S. Pat. No. 5,316,008, describes a wristwatch that features both optical and electrical sensors for measuring signals from a patient. During operation, the patient wears the wrist watch on one wrist, and places fingers from an opposing hand on the optical and electrical sensors. A pulse transit time is extracted from the signals and then used to calculate a blood pressure.

BRIEF SUMMARY OF THE INVENTION

In one aspect, the invention provides a hand-held monitoring device for measuring vital signs (e.g. blood pressure) from a patient that features: i) a housing that encloses a first sensor featuring a first electrode and a first optical system configured to generate a first optical signal; ii) a second sensor featuring a second electrode and a second optical system configured to generate a second optical signal; iii) an amplifier system, in electrical contact with the first and second electrodes, configured to processes electrical signals from the first and second electrodes to generate an electrical waveform; and iv) a microprocessor, in electrical communication with the amplifier system, first optical system, and second optical system, the microprocessor configured to process the electrical waveform and first and second optical signals (or processed versions of these signals and waveforms) with an algorithm to determine at least one of the patient's vital signs.

In preferred embodiments, the light source is an LED or diode laser configured to emit green radiation between 510 and 590 nm. Optical systems which use light sources in this spectral region are referred to herein as 'green optical systems'. In other preferred embodiments, the optical system is configured to operate in a reflection-mode geometry, e.g. both the light source and photodetector are disposed on a same side of the substrate (e.g., a printed circuit board). In this case the photodetector is aligned to detect radiation first emitted from the light source and then reflected from the patient's tissue to generate the optical waveform.

The optical system and electrodes are typically housed within a hand-held or body-worn device. In this configuration, the electrical and optical sensors are typically oriented to measure electrical and optical signals from at least one of the patient's fingers. In still other embodiments, the monitoring device additionally includes an amplifier system (e.g. a two-stage amplifier system) configured to process the first and second electrical signals to generate an electrical waveform. The device can also use this same amplifier system, or a different amplifier system, to process the optical signals to generate an optical waveform. Alternatively, the electrical and optical sensors may be housed in distinct units that are in electronic communication with the housing containing the amplifier system and the microprocessor.

Alternatively, the first and second optical systems may be replaced by other sensor systems capable of identifying a time-dependent arrival of a pulse. Examples of other sensor systems that are capable of measuring pulse waves include tonometric sensor systems, ultrasound sensor systems, magnetic field sensor systems and oscillometric cuffs. The use of one of these alternative pulse detection systems enables the identification of a first and second pulse signal that can be used in place of the first and second optical signal, and in combination with the electrical waveform and an algorithm, to calculate at least one of the patient's vital signs.

In other alternate embodiments, calibration parameters are based on biometric data, e.g., height, arm span, weight, body mass index, and age. The calibration parameters may not be specific to an individual patient, but rather determined for a general class of patients. For example, the calibration parameters are based on correlations between blood pressure and features in the optical or electrical waveforms observed in the analysis of clinical data sets. Conjunctively, the calibration parameters may be based on correlations between biometric parameters and features in the optical or electrical waveforms observed in the analysis of clinical data sets.

In embodiments, the microprocessor or microcontroller within the monitor runs computer code or 'firmware' that determines blood pressure by processing: 1) a first time-dependent feature of the optical waveform; 2) a second time-dependent feature of the electrical waveform; and 3) a calibration parameter. In this case the calibration parameter is determined by a conventional device for measuring blood pressure, such as a blood pressure cuff.

In other embodiments, the system features a first light source that emits green radiation to generate a first optical waveform, and a second light source that emits infrared radiation to generate a second optical waveform. In this case the device runs computer code or firmware that processes the first and second optical waveforms to generate a pulse oximetry value using techniques that are known in the art. In a related embodiment, the device can run computer code or firmware that processes the optical waveform to generate a heart rate value. In yet another embodiment, the device can run computer code or firmware that processes the first and second electrical signals to generate an ECG waveform, which can then be processed to calculate a heart rate.

In another aspect, the invention provides a hand-held device for measuring vital signs (e.g. blood pressure) from a patient that features: i) a housing; ii) a first optical system, enclosed by the housing, configured to generate a first optical signal; iii) a second optical system, also enclosed by the housing, configured to generate a second optical signal; and iv) a microprocessor, in electrical communication with the first optical system and second optical system, the microprocessor configured to process the first and second optical signals with an algorithm to determine at least one of the patient's vital signs.

In yet another aspect, the invention provides a hand-held device for measuring vital signs (e.g. blood pressure) from a patient that features: i) a first optical system at a first location on a subject and configured to generate a first optical signal; ii) a second optical system at a second location on a subject that is approximately mirror-symmetric about the patient's sagittal plane (i.e. a plane representing the median plane of the patient's body) to that of the first location and configured to generate a second optical signal; and iii) a microprocessor, in electrical communication with the first optical system and second optical system, the microprocessor configured to process the first and second optical signals with an algorithm to determine at least one of the patient's vital signs. Examples of locations of the first and second optical systems, respectively, include the left ear lobe and right ear lobe, the left radial artery at the subject's left wrist and the right radial artery at the subject's right wrist, any left-hand finger and any right-hand finger, any left-foot toe and any right-foot toe.

In another aspect, the invention describes a method of calculating a patient's blood pressure, comprising the steps of: i) detecting an electrical waveform corresponding to the potential difference between a first electrode at a first location on a subject and a second electrode at a second location on a subject; ii) detecting a first pulse signal on a subject and calculating a first time difference between the occurrence of a first feature on the electrical waveform and a second feature on the first pulse signal; iii) detecting a second pulse signal on a subject and calculating a second time difference between the second pulse signal and the first pulse signal; and iv) calculating the subject's blood pressure using the first time difference, the second time difference, and an algorithm relating those time differences to blood pressure. The second time difference may be calculated as a time difference between a first feature on the first pulse signal and a second pulse feature on the second pulse signal. Alternatively, the second time difference may be calculated as the time delay measured using the cross correlation between the first pulse signal and the second pulse signal. The first and second pulse signals may additionally be mathematically transformed (e.g., derivatized, averaged).

The invention has many advantages. In particular, through use of an optical system operating in a reflection-mode geometry and based on a green light source, the invention measures optical waveforms that are relatively insensitive to motion-related artifacts and have a high signal-to-noise ratio, particularly when compared to waveforms measured using red or infrared radiation in a similar geometry.

In a more general sense, the invention provides an easy-to-use, low-profile system that measures a variety of vital signs, including blood pressure, without using a cuff. This and other information can be easily transferred to a central device through a wired or wireless connection to better characterize a patient. Using the system of the invention, information describing the patient's blood pressure can be viewed using an Internet-based website, personal computer, or a mobile device. Blood-pressure information measured throughout the day provides a relatively comprehensive data set compared to that measured during isolated medical appointments. For example, this approach identifies trends in a patient's blood pressure, such as a gradual increase or decrease, which may indicate a medical condition that requires treatment.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
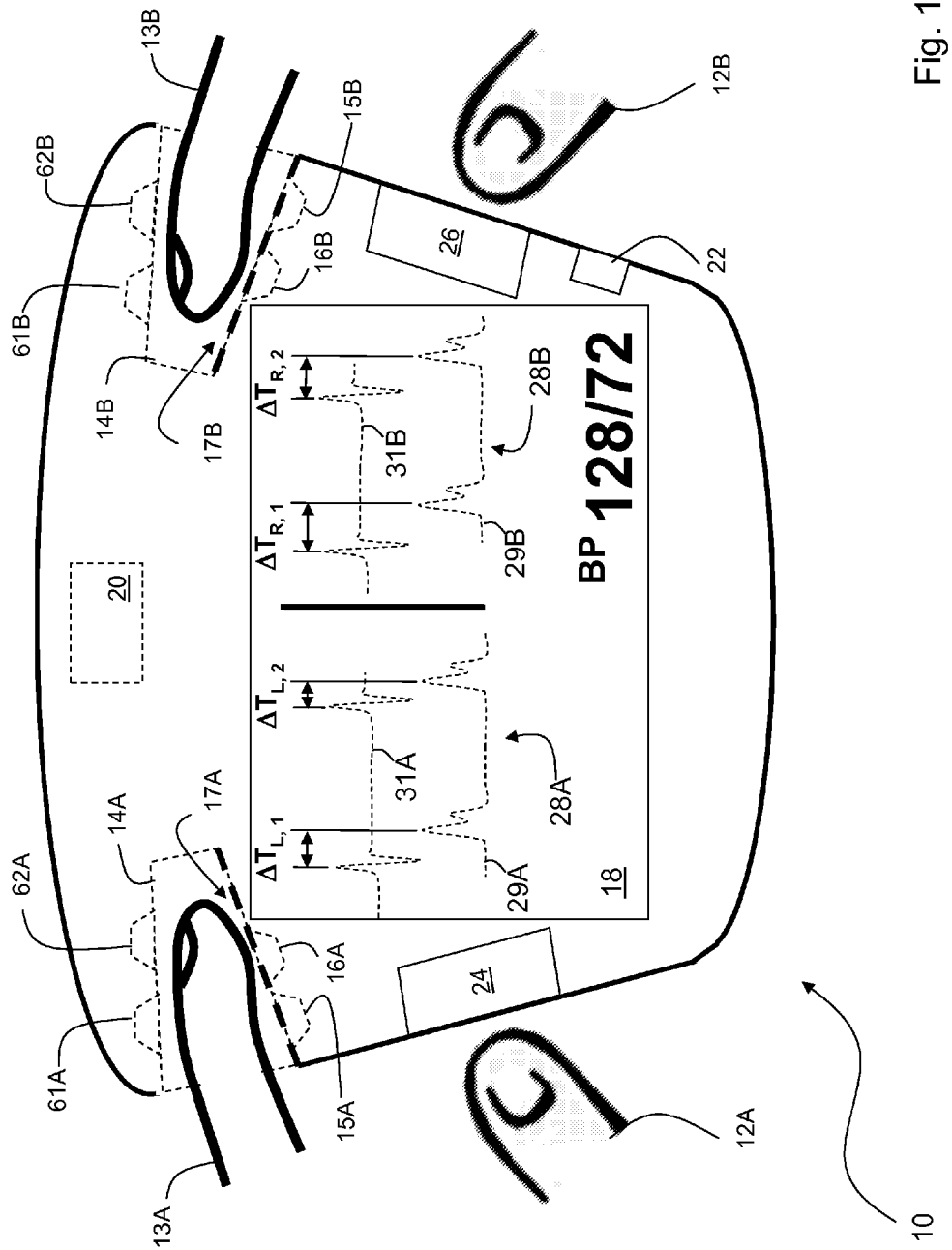
FIG. 1 is a schematic view of the hand-held monitoring device for measuring vital signs according to the invention.

FIG. 1 shows a hand-held vital signs monitoring device 10 according to the invention that measures blood pressure and other vital signs from a patient's fingers 13A, 13B (e.g., the index finger, thumb finger, etc.) using a technique referred to herein as 'bilateral pulse transit time', or BPTT. Blood pressure measured using BPTT may be more accurate than blood pressure measured using a technique based on conventional pulse transit time. To make a BPTT measurement, the patient holds the device 10 with both hands, gently inserting and pressing their left index finger 13A inside a left sensor enclosure 14A, and their right index finger 13B inside a right sensor enclosure 14B. Both the left 14A and right 14B sensor enclosures feature an LED system 15A, 15B, 61A, 61B, 62A, 62B that generates optical radiation at one or more wavelengths, and a photodetector 16A, 16B that detects radiation either reflected or transmitted from an artery in the inserted finger 13A, 13B. Each LED system 15A, 15B typically includes a green LED operating in reflection mode and red 61A, 61B and infrared 62A, 62B LEDs operating in transmission modes. An electrical system within the device detects and amplifies radiation from each index finger, as described in detail below. This generates time-resolved optical waveforms 29A, 29B, specific to each index finger, which are shown respectively on left 28A and right 28B portions of a display 18. The optical waveforms, called an 'optical plethysmograph', are described in more detail below with reference to FIGS. 3A, 3B, and 3C. Each sensor enclosure 14A, 14B also includes a conductive electrode pad 17A, 17B that measures an electrical signal when in contact with the inserted finger 13A, 13B. The electrode pad 17A, 17B, for example, can be made of metal (e.g., brass), conductive rubber, or a conventional electrode material such as silver/silver chloride. Once generated, the electrical signals are processed with an amplifier circuit and then digitized to generate an electrical waveform 31A, 31B, similar to a conventional ECG, which is also shown on the left 28A and right 28B portions of the display 18. Unlike the optical waveforms 29A, 29B, which specifically correspond to blood flowing in each index finger, a single electrical waveform 29A, 29B is determined by jointly processing electrical signals measured from each index finger using the amplifier circuit.

The device 10 measures blood pressure using BPTT by processing optical waveforms 29A, 29B and electrical waveforms 31A, 31B measured from each finger 13A, 13B or thumb 12A, 12B. Each waveform features a 'pulse' that corresponds to each of the patient's heartbeats. In the electrical waveforms 31A, 31B, this pulse represents electrical signals generated by the beating heart, and features a sharply varying feature within a conventional QRS complex of the ECG waveform. In contrast, for the optical waveforms 29A, 29B, the pulse varies more gradually and represents a time-dependent volumetric change in an underlying artery. A microprocessor in the device 10 calculates a pulse transit time ('PTT'), described in more detail with reference to FIGS. 3A, 3B, 3C, by analyzing a time difference $\Delta T$ between a point on the optical 29A, 29B and electrical 31A, 31B waveforms (e.g., the peaks of these waveforms), along with other properties described in more detail below. $\Delta T$ measured from the optical waveform 29A from the left index finger 13A and the electrical waveform 31A for two heartbeats are shown in the left-hand portion 28A of the display, and are labeled '$\Delta T_{L,1}$' and '$\Delta T_{L,2}$'. Similarly, time differences measured from the optical waveform 29B from the right index finger 13B and the electrical waveform 31B for two heartbeats are shown in the right-hand portion 28B of the display, and are labeled '$\Delta T_{R,1}$' and '$\Delta T_{R,2}$'.

Figure 2:
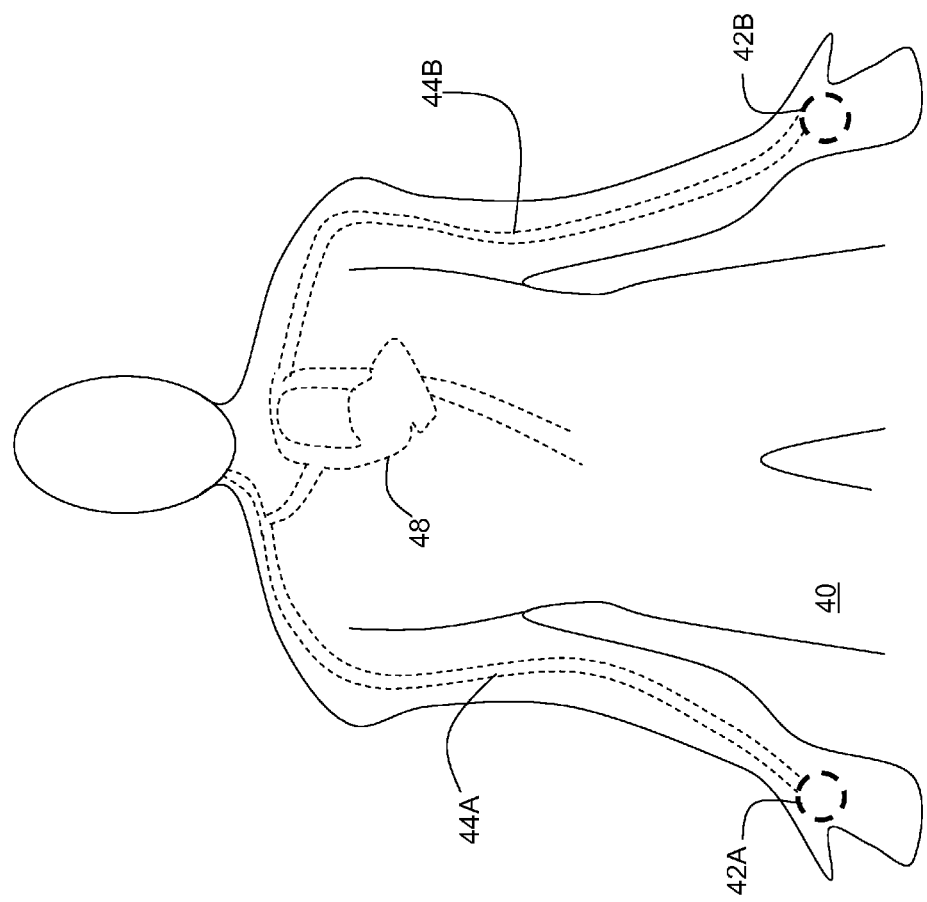
FIG. 2 is a schematic view of a patient's bilateral blood flow from the heart to the left and right sides of the body.
Figure 3:
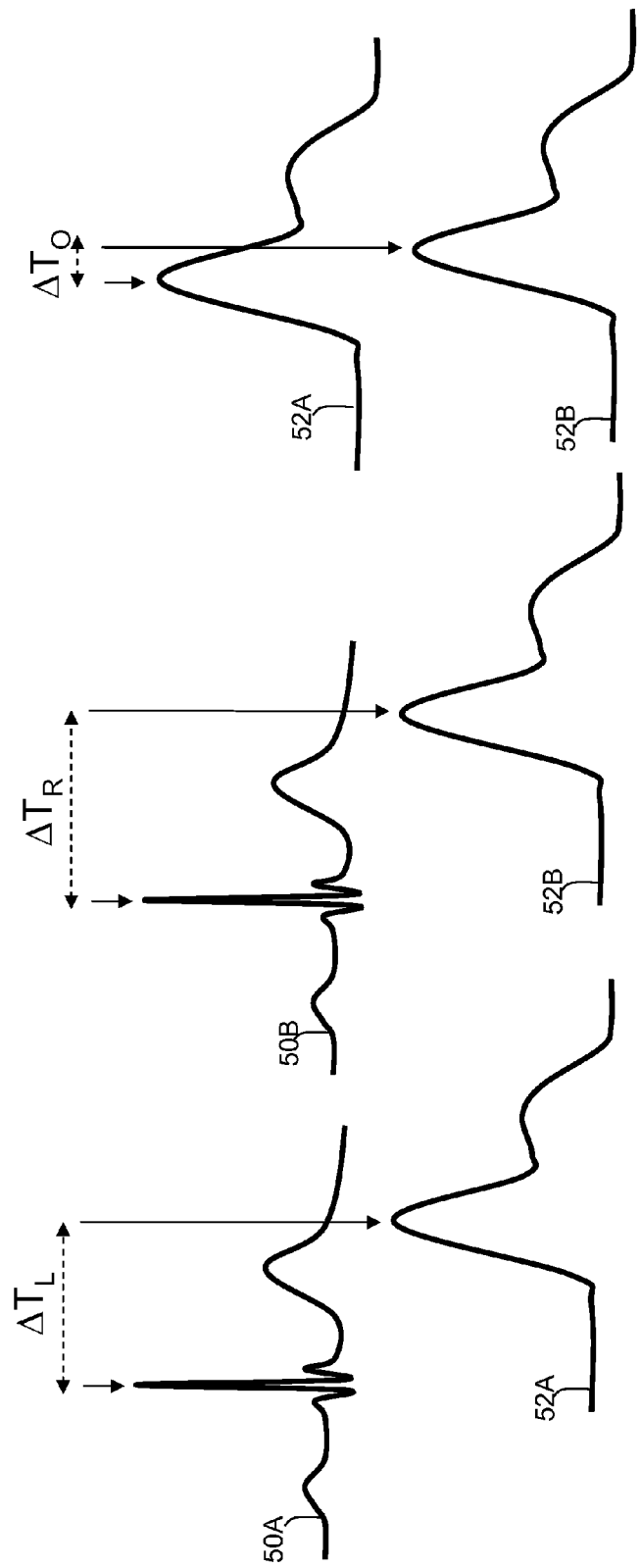
FIGS. 3A, 3B, and 3C show, respectively, graphs of optical and electrical waveforms generated with a first sensor, a second sensor, and optical waveforms generated from both the first and second sensors included in the monitor of FIG. 1.

Referring to FIGS. 2 and 3A, 3B, 3C, the hand-held device 10 measures blood pressure using BPTT by processing optical waveforms 52A, 52B and electrical waveforms 50A, 50B measured simultaneously from each side of the patient's body. Each waveform includes a 'pulse' that corresponds to each of the patient's heartbeats. In the electrical waveforms 50A, 50B, this pulse represents electrical signals generated by the beating heart, and includes a sharply varying 'peak' within a conventional QRS complex of the ECG. In contrast, for the optical waveforms 52A, 52B, the pulse varies more gradually and represents a time-dependent volumetric change in an underlying artery. A microprocessor in the device 10 calculates a pulse transit time ('PTT'), described in more detail below, by analyzing a time difference $\Delta T$ between a point on the optical 52A, 52B and electrical 50A, 50B waveforms (e.g., $\Delta T$ between the peaks of these waveforms). Specific points on the waveforms, such as their maxima or minima, can be determined by taking a first or second derivative of the waveform. $\Delta T$ measured from the optical waveform 52A from the patient's left index finger and the electrical waveform 50A is shown in FIG. 3A (labeled $\Delta T_L$). Similarly, $\Delta T$ measured from the optical waveform 52B from the right index finger and the electrical waveform 50B is shown in FIG. 3B (labeled $\Delta T_R$).

The BPTT measurement processes PTTs measured with the finger clip sensors from the patient's left finger ($\Delta T_L$) and right finger ($\Delta T_R$) to make an accurate measurement of blood pressure. Specifically, PTT depends on several factors, including blood pressure, distance between the heart and the portion of the body where the optical waveform is measured (e.g., the patient's finger), and properties of the patient's vasculature (e.g., arterial compliance, size, and stiffness).

BPTT as described herein can potentially improve the accuracy of a normal PTT measurement. For example, as shown in FIG. 2, a patient's heart 48 is typically located in a relatively well-defined position on the left-hand side of their chest cavity. With each heartbeat, blood simultaneously flows along a right-hand vascular pathlength 44A to reach a point 42A on the patient's right hand, and along a left-hand vascular pathlength 44B to reach a point 42B on the patient's left hand. The right-hand vascular pathlength 44A typically differs from the left-hand vascular pathlength 44B. The difference in pathlengths can correlate with the patient's biometric parameters (e.g., height, arm span). The difference in pathlengths and corresponding difference in PTTs can be used in the calculation of the patient's vital signs (e.g., blood pressure), as is described in more detail below.

Following a heartbeat, electrical impulses travel essentially instantaneously from the patient's heart to electrodes within each sensor enclosure (e.g., the left 14A and right 14B sensor enclosures in FIG. 1), which detect it to generate an electrical waveform. At a later time, a pressure wave induced by the same heartbeat simultaneously propagates through the patient's right-hand 44A and left-hand 44B vascular pathlengths. At points 42A, 42B on the patient's left and right hands, elastic arteries within these vascular pathlengths increase in volume due to the pressure wave. Ultimately the pressure wave arrives at a portion of the artery underneath the LED and photodetector within each sensor enclosure. These optics combine to form an optical system that detects the pressure wave by measuring a time-dependent change in optical absorption. The propagation time of the electrical impulse is independent of blood pressure, whereas the propagation time of the pressure wave depends strongly on pressure, as well as properties of the patient's arteries.

Referring again to FIGS. 3A, 3B, and 3C, during a BPTT measurement, optical sensors within the right and left sensor enclosures simultaneously measure optical waveforms 52A, 52B, while electrodes in the sensors measure electrical waveforms 50A, 50B. The optical waveforms 52A, 52B are unique to each area enclosed by the sensor enclosure, while the electrical waveforms 50A, 50B are identical, and are determined by combining electrical signals from the left and right-hand sensor enclosures. A microprocessor within the device runs an algorithm that analyzes the time difference $\Delta T_{L,R}$ between the arrivals of these signals, i.e. the relative occurrence of the optical 52A, 52B and electrical 50A, 50B waveforms for both the right-hand 44A and left-hand 44B vascular system. The microprocessor additionally analyzes the time difference $\Delta T_O$ between the arrival of the two optical signals 52A, 52B.

In a BPTT measurement, the asymmetric position of the heart, coupled with the assumption that blood pressure is equivalent along the left-hand 44B and right-hand 44A vascular pathlengths, means the PTT for the right-hand pathlength 44A will typically be slightly longer than the PTT for the left-hand pathlength 44B. This time difference, $\Delta PTT$, is the difference between $\Delta T_L$ and $\Delta T_R$ (i.e. $\Delta PTT=\Delta T_R-\Delta T_L$) and can be used to estimate the patient's arm length if a speed of the propagating pressure pulse, called a pulse wave velocity ('PWV') is assumed. Inclusion of arm length in a PTT-based measurement typically improves accuracy for both systolic and diastolic blood pressure. Use of BPTT to determine $\Delta PTT$ means arm length can be estimated without having to enter it through a software user interface. Alternatively, the arm length can be entered into a user interface associated with the monitor, and then processed along with $\Delta PTT$ to calculate a PWV. This is done by using the above-described assumptions describing the asymmetrical position of the heart. Blood pressure is known to depend strongly on PWV (typically an increase in PWV indicates an increase in blood pressure), and thus a measured PWV value can be compared to a look-up table stored in memory to calculate blood pressure. Alternatively, a mathematical algorithm, such as a predetermined relationship (e.g., a linear relationship) between PWV and blood pressure, may be used to calculate subsequent blood pressure values.

Referring to FIG. 3C, in another embodiment the time difference $\Delta T_O$ between points (e.g., peaks) on two optical signals measured from the patient's left and right hands can be processed to determine a PWV. For example, $\Delta T_O$ can be correlated to PWV and blood pressure using a predetermined relationship (e.g. a linear relationship) before making a measurement, and this correlation can be stored in a look-up table in memory on the device. The device may use an algorithm to convert $\Delta T_O$ to blood pressure for subsequent measurements.

In addition, with the BPTT measurement, optical waveforms measured from the patient's left and right hands or $\Delta PTT$ can be compared to determine slight differences in waveform shape. These slight differences can then be processed to achieve a more accurate calculation of the patient's blood pressure. For example, the differences in left and right waveform shapes or arrival times measured as described above can be used to determine a particular mathematical model for calculating blood pressure from a patient, or alternatively properties other than blood pressure. An abnormally high or negative $\Delta PTT$, for example, may indicate a profound difference between a patient's right-hand 44A and left-hand 44B vascular pathlength. Such a difference, for example, may indicate the presence of an occlusion (e.g., a blood clot) or stenosis in either vascular pathlength. In related embodiments, the $\Delta PTT$ or waveform shape differences may be used to estimate a patient's arterial compliance.

For example, the differences in the patient's right-hand 44A and left-hand 44B vascular pathlengths will result in corresponding differences in the diffusion of light-absorbing blood cells in the two pathlengths. These differences in cellular diffusion are observed as differences in the shapes of the optical waveforms 52A and 52B. The waveform shape differences will depend on the arterial compliance along the right-hand 44A and left-hand 44B vascular pathlengths. For example, the optical signals 52A, 52B shown in FIGS. 3A, 3B, 3C typically feature a main peak and a secondary peak, where the secondary peak is typically classified as a 'dichrotic notch'. Studies published in the literature describe how the dichrotic notch, particularly when analyzed by taking a second derivative of the plethysmogram, relates to vascular compliance (see, e.g., 'Assessment of Vasoactive Agents and Vascular Aging by the Second Derivative of Photoplethysmogram Waveform', Takazawa et. al, Hypertension 32: 365-370, 1998; the contents of which are incorporated herein by reference). Arterial compliance determined using this or another method can then be used to group patients having similar arterial properties. An algorithm can then process $\Delta PTT$ or PWV values for patients in a particular group, or compare these values to predetermined look-up tables, to make a blood pressure measurement. For example, the algorithm may use a predetermined relationship (e.g. a linear relationship) between PWV or $\Delta PTT$ and blood pressure to calculate subsequent blood pressure values.

Referring again to FIGS. 3A, 3B, and 3C, in yet another embodiment, processing the electrical waveform 50A, 50B and optical waveforms 52A, 52B can be used to estimate a property called pre-ejection period ('$\Delta T_{PEP}$'), which is the time delay between the beginning of a patient's heart beat and the beginning of the patient's cardiac stroke. Specifically, both $\Delta T_R$ and $\Delta T_L$ depend on $\Delta T_{PEP}$ and the time it takes the pressure pulse to leave the heart and arrive at the optical system underneath a corresponding sensor. As shown in FIG. 3C, this time difference, referred to as $\Delta T_O$, can be measured directly from sensors located near the patient's heart and finger. If the sensor is located on the patient's right hand, $\Delta T_R-\Delta T_O=\Delta T_{PEP}$, while if the sensor is located on the patient's left hand $\Delta T_L-\Delta T_O=\Delta T_{PEP}$. $\Delta T_{PEP}$ correlates with the patient's systolic function, with a shorter $\Delta T_{PEP}$ typically indicating a relatively healthy systolic function. A measured $\Delta T_{PEP}$ can be used in conjunction with the time difference between a feature on the electrical waveform and one or more features on one or more optical waveforms to improve the accuracy of the calculated PTT and corresponding blood pressure. In particular, it has been shown in previous studies that systolic blood pressure can correlate better to a $\Delta PTT$ value, whereas diastolic blood pressure and mean arterial blood pressure can correlate better to a $\Delta PTT$ value corrected for $\Delta T_{PEP}$, i.e. $\Delta PTT-\Delta T_{PEP}$ (see, e.g., 'Pulse transit time measured from the ECG: an unreliable marker of beat-to-beat blood pressure', Payne et. al, J. Appl. Physiol 100: 136-141, 2006; the contents of which are incorporated herein by reference). $\Delta T_{PEP}$ values may also vary with respiration and inspiration, thereby affecting the measured blood pressure. For this reason, in embodiments, computer code operating in the monitor described above can first process two optical waveforms to estimate $\Delta T_{PEP}$. Once this is done, the computer code can determine $\Delta PTT$ and $\Delta PTT-\Delta T_{PEP}$, which are then used to calculate, respectively, systolic and diastolic blood pressure.

Figure 4:
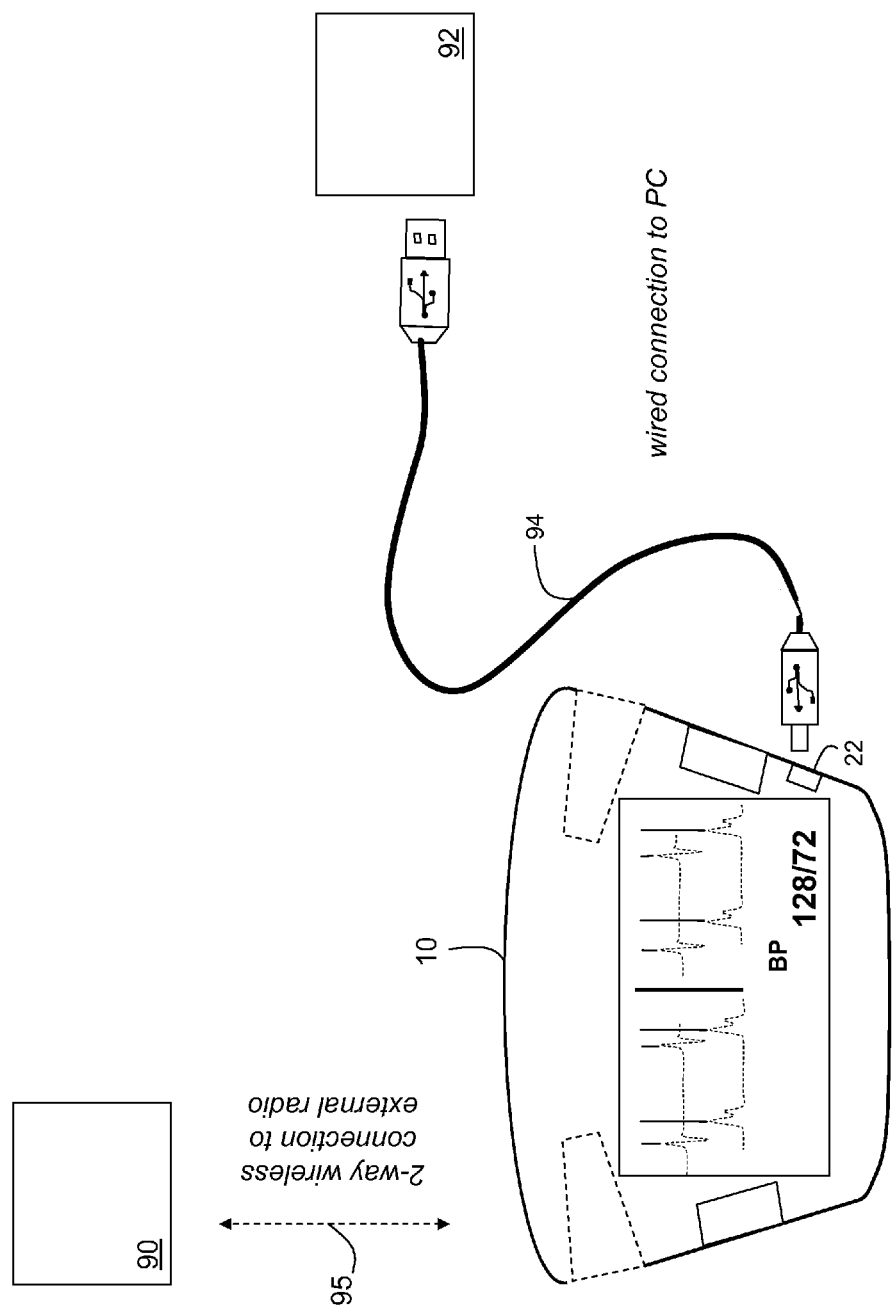
FIG. 4 is a semi-schematic view of the monitoring device of FIG. 1 connected to a personal computer through a USB port or to an external radio through a wireless connection; and, FIG. 5 is a schematic view of an Internet-based system that receives information from the monitoring device of FIG. 1 through a wireless connection.

Referring to FIG. 4, to transfer information to Internet-accessible devices, the device 10 includes a mini USB port 22 that connects to a personal computer 92 through a conventional USB connector terminating a first cable 94. Alternatively, the device 10 connects to an external radio 90 through a 2-way radio connection. The external radio 90, for example, could be within the personal computer 92 or another device, such as a scale, chest strap, or additional monitor.

Figure 5:
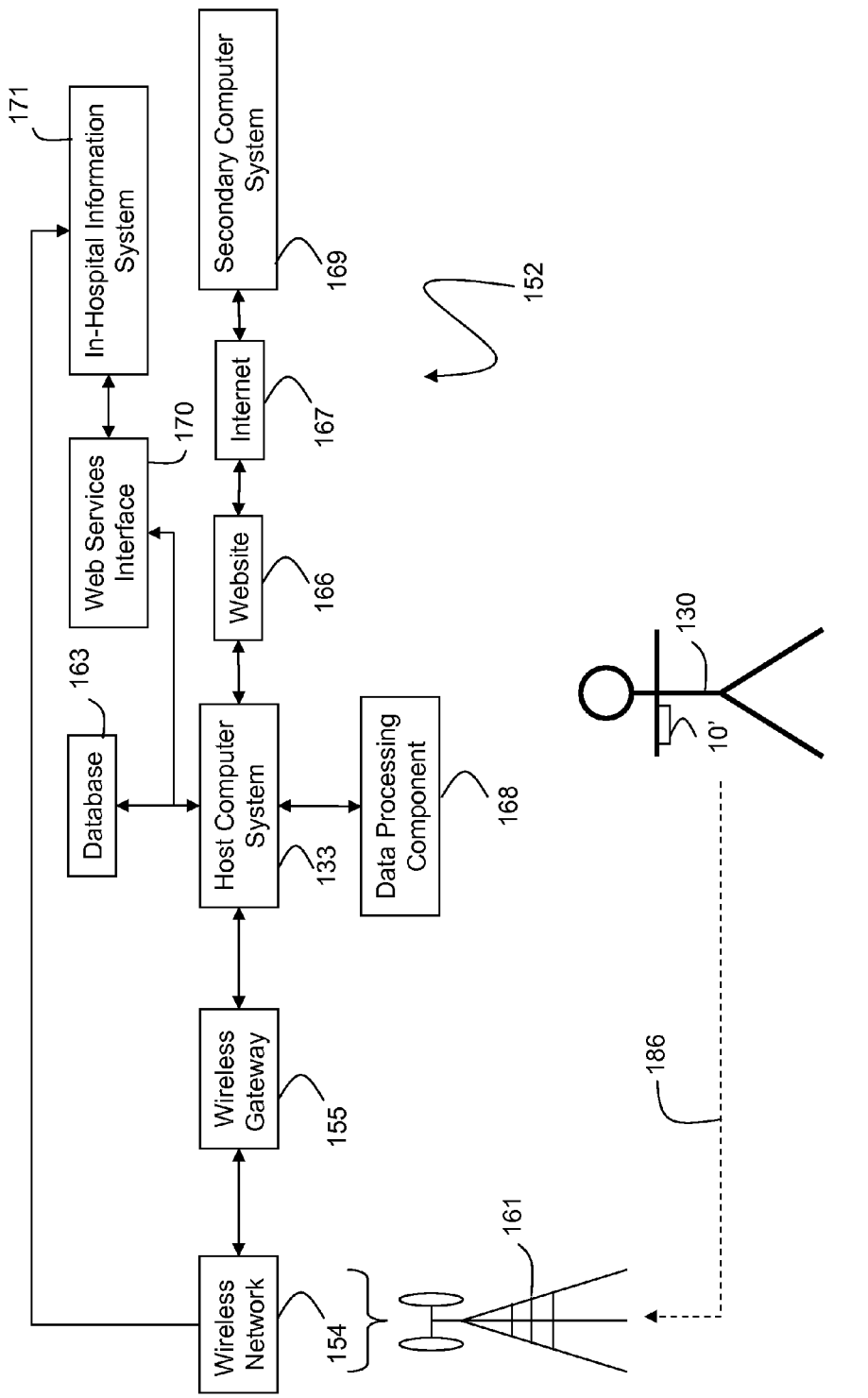

FIG. 5 shows a preferred embodiment of an Internet-based system 152 that operates in concert with the device 10 and to send information from a patient 130 to an in-hospital information system 171 (e.g., a system for electronic medical records). During operation, the device 10 collects vital sign information from the patient 130 and, using an internal radio as described above, transmits information through a wireless interface 186 to a wireless network 154 (e.g., either a nationwide or local wireless network), and from there to a web site 166 hosted on an Internet-based host computer system 133. A secondary computer system 169 accesses the website 166 through the Internet 167. A wireless gateway 155 connects to the host computer system 133 and ultimately to the wireless network 154, and receives data from one or more monitors, as discussed below. The host computer system 133 includes a database 163 and a data-processing component 168 for, respectively, storing and analyzing data sent from the monitor. The host computer system 133, for example, may include multiple computers, software systems, and other signal-processing and switching equipment, such as routers and digital signal processors. The wireless gateway 155 preferably connects to the wireless network 154 using a TCP/IP-based connection, or with a dedicated, digital leased line (e.g., a VPN, frame-relay circuit or digital line running an X.25 or other protocols). The host computer system 133 also hosts the web site 166 using conventional computer hardware (e.g. computer servers for both a database and the web site) and software (e.g., web server and database software). To connect to the in-hospital information system 171, the host computer system 133 typically includes a web services interface 170 that sends information using an XML-based web services link to a computer associated with the in-hospital information system 171. Alternatively, the wireless network 154 may be an in-hospital wireless network (e.g., a network operating Bluetooth™, 802.11a, 802.11b, 802.1g, 802.15.4, or 'mesh network' wireless protocols) that connects directly to the in-hospital information system 171. In this embodiment, a nurse working at a central nursing station can quickly view the vital signs of the patient using a simple computer interface.

To view information remotely, the patient or medical professional can access a user interface hosted on the web site 166 through the Internet 167 from a secondary computer system 169, such as an Internet-accessible home computer. The system may also include a call center, typically staffed with medical professionals such as doctors, nurses, or nurse practitioners, whom access a care-provider interface hosted on the same website 166.

The device 10 can optionally be used to determine the patient's location using embedded position-location technology (e.g., GPS, network-assisted GPS, or Bluetooth™, 802.11-based location system). In situations requiring immediate medical assistance, the patient's location, along with relevant vital sign information, can be relayed to emergency response personnel.

We claim as our invention:

1. A method for calculating blood pressure from a patient, said method comprising:
   detecting an electrical waveform corresponding to the electrical activity of the patient's heart with a first sensor comprising a first electrode located at a first location on a subject and a second electrical signal measured by a second electrode located at a second location on the subject, the first and second electrodes operably connected to an amplifier system that generates the electrical waveform from the electrical activity which is detected by the first and second waveforms;
   detecting a first pulse waveform with a second sensor located on a hand of the subject;
   detecting a second pulse waveform with a third sensor located on the opposite hand of the subject;
   transmitting the electrical waveform, the first pulse waveform, and the second pulse waveform to a microprocessor; and
   processing the electrical waveform, the first pulse waveform, and the second pulse waveform by using the microprocessor to (i) identify a first feature in the electrical waveform corresponding to a heartbeat, (ii) identify a second feature in the first pulse waveform corresponding to the heartbeat, (iii) identify a third feature in the second pulse waveform corresponding to the heartbeat, (iv) calculate a first time difference between the first feature and the second feature, (v) calculate a second time difference between the first feature and the third feature; (vi) calculate a third time difference between the first time difference and the second time difference and (vii) calculate the subject's blood pressure using the third time difference and an algorithm relating the third time difference to blood pressure.

2. The method of claim 1, wherein the the second and third sensor each comprises an optical system configured to generate a photoplethysmogram.

3. The method of claim 2, wherein the optical system comprises a light source and a photodetector on a common substrate.

4. The method of claim 3, wherein the photodetector is configured to receive radiation from the light source after it reflects off one of the patient's fingers.

5. The method of claim 1, wherein the first and second pulse waveform are each an optical waveform.

6. The method of claim 1, further comprising calculating a blood pressure with a microprocessor configured to process at least one of the electrical waveform and first optical signal, or at least one derivative thereof, to determine a heart rate.

7. The method of claim 1, further comprising transmitting information with a wireless system configured to wirelessly transmit at least one of the patient's vital signs to an external receiver.

* * * * *